United States Patent
Kong et al.

(10) Patent No.: US 10,314,811 B2
(45) Date of Patent: Jun. 11, 2019

(54) COMPOSITIONS AND METHODS FOR SELECTIVELY INHIBITING INTESTINAL CARBOXYLESTERASE 2 ENZYME ACTIVITY

(71) Applicant: The Methodist Hospital, Houston, TX (US)

(72) Inventors: Ren Kong, Jiangsu (CN); Hong Zhao, Missouri City, TX (US); Stephen T. C. Wong, Houston, TX (US)

(73) Assignee: The Methodist Hospital, Houston, TX (US)

( * ) Notice: Subject to any disclaimer, the term of this patent is extended or adjusted under 35 U.S.C. 154(b) by 0 days.

(21) Appl. No.: 15/754,133

(22) PCT Filed: Aug. 18, 2016

(86) PCT No.: PCT/US2016/047544
§ 371 (c)(1),
(2) Date: Feb. 21, 2018

(87) PCT Pub. No.: WO2017/034919
PCT Pub. Date: Mar. 2, 2017

(65) Prior Publication Data
US 2018/0235928 A1 Aug. 23, 2018

Related U.S. Application Data

(60) Provisional application No. 62/208,225, filed on Aug. 21, 2015.

(51) Int. Cl.
| | |
|---|---|
| *A61K 9/00* | (2006.01) |
| *A61P 1/12* | (2006.01) |
| *A61K 31/12* | (2006.01) |
| *A61K 45/06* | (2006.01) |
| *A61K 31/121* | (2006.01) |
| *A61K 31/352* | (2006.01) |
| *A61K 31/353* | (2006.01) |
| *A61K 31/4745* | (2006.01) |

(52) U.S. Cl.
CPC .......... *A61K 31/352* (2013.01); *A61K 9/0053* (2013.01); *A61K 31/12* (2013.01); *A61K 31/121* (2013.01); *A61K 31/353* (2013.01); *A61K 31/4745* (2013.01); *A61K 45/06* (2013.01); *A61P 1/12* (2018.01)

(58) Field of Classification Search
None
See application file for complete search history.

(56) References Cited

U.S. PATENT DOCUMENTS

2003/0211180 A1  11/2003  Cheng et al.
2017/0246190 A1*  8/2017  Liao ..................... A61K 31/353

FOREIGN PATENT DOCUMENTS

WO    WO 2008/035208    3/2008

OTHER PUBLICATIONS

Trivedi et al., Food and Chemical Toxicology (2011), 49(4), pp. 838-847.*
Trivedi et al., Cardiovascular Toxicology (2011), 11(3), pp. 215-225.*
Hatkevich et al., Experimental Cell Research (2014), 327(2), 331-339.*
Orlikova, et al., "Dietary chalcones with chemopreventive and chemotherapeutic potential", Genes Nutr. May 2001; 6(2): 125-147.
Orsolic, et al., "Protective effects of propolis and related polyphenolic/flavonoid compounds against toxicity induced by irinotecan", Med. Oncol. (2010) 27:1346-1358.
Bansal et al "Pre-Clinical Evidence for Altered Absorption and Biliary Excretion of Irinotecan (CPT-11) in Combination with Quercetin: Possible Contribution of P-Glycoprotein" Life Sciences vol. 83, pp. 250-259, 2008.
Imai et al "Phytoestrogens/Flavonoids Reverse Breast Cancer Resistance Protein/ABCG2-Mediated Multidrug Resistance" Cancer Research vol. 64, pp. 4346-4352, 2004.
Lou et al "Naringenin Decreases Invasiveness and Metastasis by Inhibiting TGF-β-Induced Epithelial to Mesenchymal Transition in Pancreatic Cancer Cells" PLoS One vol. 7, pp. 1-9, 2012.
Mohan et al "Combinations of Plant Polyphenols and Anti-Cancer Molecules: A Novel Treatment Strategy for Cancer Chemotherapy" Anti-Cancer Agents in Medicinal Chemistry vol. 13, pp. 281-295, 2013.
Takahata et al "Chemosensitivity Determinants of Irinotecan Hydrochloride in Hepatocellular Carcinoma Cell Lines" Basic and Clinical Pharmacology and Toxicology vol. 102, pp. 399-407, 2007.

* cited by examiner

*Primary Examiner* — Brian J Davis
(74) *Attorney, Agent, or Firm* — Cesari and McKenna, LLP

(57) ABSTRACT

A method for treating diarrhea induced by a chemotherapy agent by administering a carboxylesterase 2 (CES2) inhibitor, i.e., hesperetin, naringenin, or 2',4'-dihydroxychalcone. Also disclosed is a method for treating cancer by administering a chemotherapy agent together with hesperetin, naringenin, or 2',4'-dihydroxychalcone. Furthermore, a composition for treating cancer is provided, the composition containing a chemotherapy agent and hesperetin, naringenin, or 2',4'-dihydroxychalcone.

25 Claims, 4 Drawing Sheets

COMPOSITIONS AND METHODS FOR SELECTIVELY INHIBITING INTESTINAL CARBOXYLESTERASE 2 ENZYME ACTIVITY

CROSS-REFERENCE TO RELATED APPLICATIONS

The present application is the National Stage of International Application No. PCT/US2016/047544, filed on Aug. 18, 2016, which claims the benefit of U.S. Provisional Patent Application Serial No. 62/208,225 filed on Aug. 21, 2015. The contents of both applications are hereby incorporated by reference in their entirety.

BACKGROUND

Camptothecin (CPT)-derived drugs, such as irinotecan (CPT-11), are typically used for treating solid brain, colon, and lung tumors, as well as for treating refractory forms of leukemia and lymphoma. See Pommier Nat. Rev. Cancer, 6(10):789 802.

The antineoplastic efficacy of CPT-11 is limited by a delayed diarrhea that occurs about 2 to 4 days after administration. Severe diarrhea induced by CPT-11 and other camptothecin-derived drugs has significant negative medical consequences, especially for the elderly. The onset of diarrhea necessitates a reduction in CPT-11 dosage or even a complete halt of therapy until the patient's intestinal function returns to normal.

The mechanism of CPT-11-induced diarrhea has been the subject of intensive study. CPT-11, which is a prodrug, is hydrolyzed by carboxylesterases in the liver to its therapeutically active form, 7-ethyl-10 hydroxycamptothecin (SN-38). SN-38 undergoes further metabolism in both the liver and intestines, where it is conjugated with glucuronic acid to form the inactive compound, SN-38G. CPT-11, SN-38, and SN-38G are then eliminated via the gastrointestinal tract in bile.

The highly expressed carboxylesterase (CES) 2 in the intestine effectively converts CPT-11 to SN-38 with a potency 100-fold higher than its liver homolog, CES1. The conversion results in a high local concentration of toxic SN-38 in the intestinal lumen, causing damage to intestinal epithelial cells and subsequent diarrhea.

Several compounds have been recently identified that show a high selectivity for inhibiting CES2 as compared to CES1. See Stoddard et al. 2010, J. Pest. Sci., 35(3):240-249; Hatfield et al. 2011, Expert Opin. Ther. Pat., 21(8):1159-117). However, these compounds have low solubility and poor pharmaceutical properties.

There is a need to identify improved selective CES2 inhibitors that can ameliorate diarrhea induced by CPT-11 administered for treating cancer.

SUMMARY

To meet the need set forth above, a method for treating diarrhea induced by a chemotherapy agent is provided. The method includes administering to a subject a therapeutically effective amount of a carboxylesterase 2 (CES2) inhibitor. The CES2 inhibitor is selected from hesperetin, naringenin, and 2',4'-dihydroxy-chalcone.

Also disclosed is a method for treating cancer by administering a chemotherapy agent together with a CES2 inhibitor selected from hesperetin, naringenin, and 2',4'-dihydroxychalcone.

Further, a composition for treating cancer is provided. The composition contains a chemotherapy agent and a CES2 inhibitor selected from the group consisting of hesperetin, naringenin, and 2',4'-dihydroxychalcone.

The details of one or more embodiments of the invention are set forth in the drawings and description below. Other features, objects, and advantages of the invention will be apparent from the description and from the claims.

Importantly, all references cited herein are hereby incorporated by reference in their entirety.

BRIEF DESCRIPTION OF THE DRAWINGS

The description below refers to the accompanying drawings, of which.

DETAILED DESCRIPTION

Figure 1A:
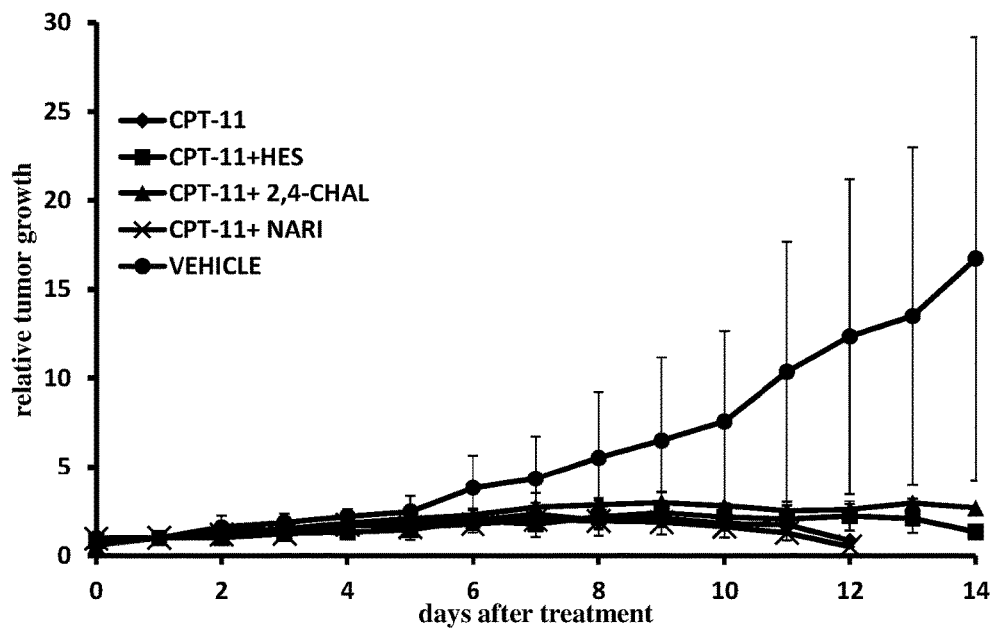
FIG. 1A is a plot of relative tumor growth in tumor-bearing mice versus day after initiation of treatment with the indicated regimens. Error bars represent standard error of the mean (SEM). CPT-11=irinotecan, HES=hesperetin, 2,4-CHAL=2',4'-dihydroxychalcone, NARI=naringenin.

As mentioned above, a method for treating diarrhea induced by a chemotherapy agent is disclosed.

The chemotherapy agent can be, e.g., any agent that is rendered toxic in the intestines by the enzymatic activity of CES2. For example, the chemotherapy agent can be a camptothecin analogue.

More specifically, the camptothecin analogue is irinotecan, topotecan, 7-ethyl-10 hydroxycamptothecin (SN-38), liposomal encapsulated SN-38, polyethylene glycol-conjugated SN-38, PEG-polyglutamic acid micelle encapsulated SN-38, or PEG-cyclodextrin encapsulated SN-38.

As an alternative, the chemotherapy agent can be capecitabine or LY2334737, a pro-drug of gemcitabine.

The method requires administering an effective amount of a CES2 inhibitor selected from hesperetin, naringenin, and 2',4'-dihydroxychalcone.

In a particular embodiment of the method, the chemotherapy agent is irinotecan and the CES2 inhibitor is hesperetin.

The method described above can further include administering an anti-emetic agent, an anti-motility agent, or a combination of these agents.

Anti-emetic agents that can be administered in the method include, but are not limited to, 5-hydroxytryptamine-3 receptor antagonists (e.g., dolasetron, tropisetron and granisetron), dopamine antagonists (e.g., domperidone and olanzapine), neurokinin-1 receptor antagonists (e.g., aprepitant), antihistamines (e.g., diphenhydramine), cannabinoids, benzodiazepines, anticholinergics, and steroids.

Anti-motility agents that can be used in the method of the invention can be. e.g., loperamide, diphenoxylate, paregoric tincture of opium, codeine, and morphine.

In one example, a CES2 inhibitor is administered together with loperamide. In another example, the CES2 inhibitor is administered together with dolasetron.

The method set forth above can include administering two different CES2 inhibitors. The two different CES2 inhibitors can both be selected from hesperetin, naringenin, and 2',4'-dihydroxychalcone. For example, hesperetin can be co-administered with 2',4'-dihydroxychalcone.

Alternatively, one CES2 inhibitor selected from hesperetin, naringenin, and 2',4'-dihydroxychalcone can be administered together with a bacterial beta glucuronidase (β-GUS) inhibitor. Not to be bound by theory, it is believed that inhibition of β-GUS activity in intestinal microbiota blocks the removal of a glucuronide group from SN-38G, thereby preventing the formation of cytotoxic SN-38 in the intestines.

Exemplary β-GUS inhibitors include amoxapine, mefloquine, nialamide, isocarboxazid and phenelzine. See Ahmad et al. 2012, J. Biomol. Screen. 17: 957-965. In a specific example, hesperetin is administered together with amoxapine.

As set forth, supra, a method is also provided for treating cancer with a chemotherapy agent and a CES2 inhibitor.

The chemotherapy agent administered in this method can be a camptothecin analogue. More specifically, the camptothecin analogue can be irinotecan, topotecan, SN-38, liposomal encapsulated SN-38, polyethylene glycol-conjugated SN-38, PEG-polyglutamic acid micelle encapsulated SN-38, and PEG-cyclodextrin encapsulated SN-38.

The CES2 inhibitor administered in this method can be hesperetin, naringenin, or 2',4'-dihydroxychalcone.

The chemotherapy agent can be administered via the same route as the CES2 inhibitor. In an exemplary method of the invention, both the chemotherapy agent and the CES2 inhibitor are administered orally.

Alternatively, the chemotherapy agent is administered via a different route than the CES2 inhibitor. An exemplary method includes administering a camptothecin analogue by infusion and administering the CES2 inhibitor orally.

In one embodiment of the method, the chemotherapy agent is irinotecan and the CES2 inhibitor is hesperetin. In one example, irinotecan is administered by infusion and hesperetin is administered orally. In another example, irinotecan and hesperetin are both administered orally.

The method for treating cancer can also include administering, together with a chemotherapy agent and a CES2 inhibitor, an anti-emetic agent, an anti-motility agent, or a combination of these agents. Any of the anti-emetic agents and anti-motility agents described above can be administered.

In one example, a chemotherapy agent and a CES2 inhibitor are administered together with loperamide. In another example, the chemotherapy agent and CES2 inhibitor are administered together with dolasetron.

In certain embodiments, the method includes administering two different CES2 inhibitors. The two different CES2 inhibitors can both be selected from hesperetin, naringenin, and 2',4'-dihydroxychalcone.

As an alternative, a chemotherapy agent and one CES2 inhibitor selected from hesperetin, naringenin, and 2',4'-dihydroxychalcone are administered together with a β-GUS inhibitor, such as those described, supra. In a specific example, irinotecan and hesperetin is administered together with amoxapine.

A composition is also provided for treating cancer. The composition contains a chemotherapy agent and a CES2 inhibitor selected from the group consisting of hesperetin, naringenin, and 2',4'-dihydroxychalcone.

The chemotherapy agent is preferably a camptothecin analogue. The camptothecin analogue can be, but is not limited to, irinotecan, topotecan, SN-38, liposomal encapsulated SN-38, polyethylene glycol-conjugated SN-38, PEG-polyglutamic acid micelle encapsulated SN-38, and PEG-cyclodextrin encapsulated SN-38.

The invention also encompasses the use of a CES2 inhibitor selected from hesperetin, naringenin, and 2',4'-dihydroxychalcone for treating chemotherapy-induced diarrhea.

Furthermore, the use of a chemotherapy agent together with hesperetin, naringenin, or 2',4'-dihydroxychalcone for treating cancer is also within the scope of the invention.

Without further elaboration, it is believed that one skilled in the art can, based on the disclosure herein, utilize the present disclosure to its fullest extent. The following specific examples are to be construed as merely descriptive, and not limitative of the remainder of the disclosure in any way whatsoever.

EXAMPLE 1

Repositioning of Drugs for Treating Diarrhea

An integrated platform including in silico screening, enzyme based assays, and animal testing was exploited to identify specific CES2 inhibitors among known drugs.

Based on the homology modeling structure of CES2, a molecular docking approach was employed to facilitate in silico screening against several chemical libraries of known drugs, including Prestwick library, Johns Hopkins Clinical Compound Library, LOPAC1280, and MicroSource Spectrum Collection.

Although the protein structure of CES2 is currently unavailable, a panel of CES1 crystal structures in apo form or in complex with a substrate has been resolved. The amino acid sequences of CES1 and CES2 share 47% identical residues and 58% conserved residues, indicating that a reliable structural model of CES2 could be built based on the CES1 structure. A homology structure of CES2 based on the complex structure of CES1 with pdb code of 1MX1 was built. Energy minimization was used to refine the homology model by using Prime module from Schrodinger. The refined structure was used as the receptor for virtual screening to identify chemically diverse putative CES2 inhibiting drugs.

The standard precision mode of Glide software was used to explore the binding of all the drugs with the active site of CES2 centered on conserved catalytic residue S228. In this way, the empirical Glide score was derived to approximate the binding affinity and rank the drugs. In addition, the complementary Molecular Mechanics—Generalized Born Surface Area method (MMGBSA) was included to score the putative inhibitors as well. See Hou et al. 2011, J. Chem. Inf. Model. 51(1): 69-82.

A visual inspection was performed on the top 10% ranked drugs. Several criteria were taken into consideration in drug selection: 1) high ranking either in Glide score or in MMGBSA score, 2) binding at or near the active site, and 3) structural diversity among the selected drug molecules. The selected drugs were expected to be validated by in vitro testing as potential CES2 inhibitors.

The binding poses of three compounds, i.e., hesperetin, naringenin, and 2',4'-dihydroxychalcone, were extracted from the docking results. All three compounds were predicted to bind inside the active site of CES2 near catalytic residues, H457 and S228.

EXAMPLE 2

Enzyme-Based Assays

CES2 and CES1 enzyme assays were used for primary screening and $IC_{50}$ determination of potential inhibitors. The assays are well established and widely used in compound discovery and lead optimization for CES inhibitors. See, e.g., Wadkins et al. 2004, Mol. Pharmacol. 65(6):1336 1343; Wadkins et al. 2005, J. Med. Chem. 48(8):2906 2915; Hicks et al. 2009, J. Med. Chem. 52(12):3742 3752; Hyatt et al. 2007, J. Med. Chem. 50(8):1876 1885; Hicks et al. 2007, Bioorg. Med. Chem. 15(11):3801 3817; Hyatt et al. 2007, J. Med. Chem., 50(23):5727 5734; Wadkins et al. 2007, Mol. Pharmacol. 71(3):713 723; and Young et al. 2010, J. Med. Chem., 53(24):8709 8715. CES converts esters into the corresponding alcohol and carboxylic acid. The esterase substrate, 4 nitrophenyl acetate (4 NPA), was used to detect enzyme activity. The recombinant purified intestinal CES2 and human liver CES1 enzymes and 4 NPA were purchased from Sigma Aldrich (product ID E0412, E0162, and N8130, respectively). All test compounds were dissolved in DMSO at 10 mM, and diluted in 50 mM HEPES to different concentrations for $IC_{50}$ determination. The assays were conducted in a total volume of 300 µL in 96 well microtiter plates. Reaction mixtures consisted of the following: 100 µL 50 mM HEPES with 10 units of enzyme, 10 µL compound solution (various concentrations), 2 µL 300 mM 4 NPA and 188 µL 50 mM HEPES, pH 7.4. The test compound and 4 NPA solution were added to the wells first and then the reaction was initiated by the addition of enzyme solution. After incubation for 15 min. at 25° C., absorbance at 405 nm was measured using a microplate reader. The results are shown in Table 1 below.

TABLE 1

In vitro efficacy and selectivity of active compounds

| Compound | $IC_{50}$ CES2 Assay (µM) | $IC_{50}$ CES1 Assay (µM) | Selectivity ($IC_{50}$ CES1)/($IC_{50}$ CES2) |
|---|---|---|---|
| hesperetin | 2.54 | >300 | >118 |
| naringenin | 9.72 | 158.70 | 16.33 |
| 2',4' dihydroxy-chalcone | 1.66 | >300 | >180 |

The enzyme based assays showed that hesperetin, naringenin, and 2',4' dihydroxychalcone selectively inhibited CES2 activity with $IC_{50}$ values of 2.54 µM, 9.72 µM, and 1.66 µM, respectively. No significant inhibition of CES1 was seen for hesperetin and 2',4' dihydroxychalcone, using concentrations of these two drugs as high as 300 µM. This corresponds to greater than 100-fold selectivity for CES2 over CES1. Naringenin demonstrated a lower but still considerable fold selectivity of 16.33.

EXAMPLE 3

In Vivo Testing of Anti-Diarrheal Activity

The anti-diarrheal activity of hesperetin, naringenin and 2',4' dihydroxy-chalcone was tested in tumor bearing mice by administering these three drugs orally together with daily intraperitoneal (i.p.) injections of CPT-11.

CPT-11 was purchased from Selleck Chemicals. To obtain an injectable formulation, CPT-11 (20 mg/mL) was dissolved in a solution containing D sorbitol (45 mg/mL) and D lactic acid (0.9 mg/mL) in $ddH_2O$, and heated to ~70° C. to 90° C. for 5 to 10 min See Trifan et al. 2002, Cancer Res., 62(20):5778 5784. The pH of the solution was adjusted to 3.5 prior to sterile filtration. The solution was stored protected from light until just prior to administration.

Hesperetin, naringenin, and 2',4' dihydroxychalcone were purchased from MicroSource. Each of these compounds was dissolved separately in 100% DMSO and then diluted into a 0.5% carboxymethylcellulose solution. The final concentration of DMSO was less than 1%.

Healthy 6-8 week old female Balb/cJ mice were obtained from Jackson Laboratories (Bar Harbor, Me. USA). CT 26 tumor cells, derived from a murine Balb/c colon adenocarcinoma, were used to form tumors by subcutaneous injection of tumor cells into the posterior mid-dorsum of the mice. When tumors reached ~500 $mm^3$ (~10 days after implantation, defined as day 1), treatment was initiated. The mice were divided into five groups of 3-4 animals each and treated as follows:

(1) Vehicle group, mice received an equivalent volume of CPT-11 vehicle i.p. from day 1 to day 10, and an equivalent volume of compound vehicle orally from day 0 to day 11;

(2) CPT-11 only group, mice received CPT-11 (50 mg/kg) i.p. from day 1 to day 10, and an equivalent volume of compound vehicle orally from day 0 to day 11;

(3) CPT-11+hesperetin group, mice received CPT-11 (50 mg/kg) i.p. from day 1 to day 10, and hesperetin solution (40 mg/kg) orally from day 0 to day 11;

(4) CPT-11+naringenin group, mice received CPT-11 (50 mg/kg) i.p. from day 1 to day 10, and naringenin solution (40 mg/kg) orally from day 0 to day 11; and (5) CPT-11+2',4' dihydroxychalcone group, mice received CPT-11 (50 mg/kg) i.p. from day 1 to day 10, and 2',4' dihydroxychalcone solution (40 mg/kg) orally from day 0 to day 11.

CPT-11 and the CES2 inhibitors were each administrated once per day during the experiment.

Figure 1B:
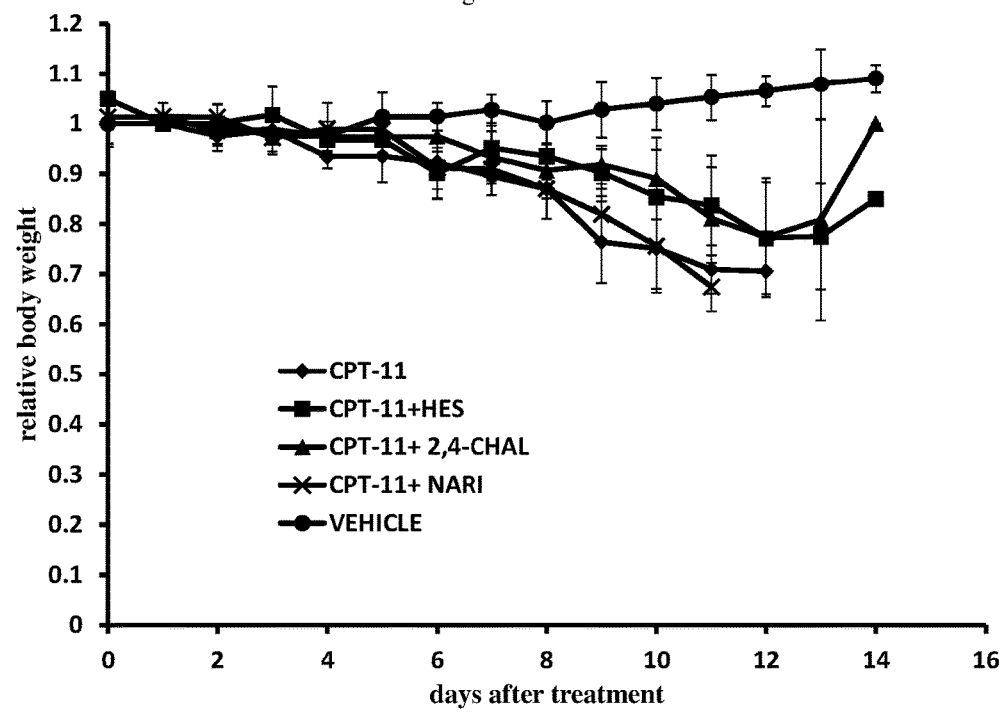
FIG. 1B is a plot of relative body weight in the tumor-bearing mice versus day after initiation of treatment with the indicated regimens. Error bars represent SEM. CPT-11=irinotecan, HES=hesperetin, 2,4-CHAL=2',4'-dihydroxychalcone, NARI=naringenin.
Figure 1C:
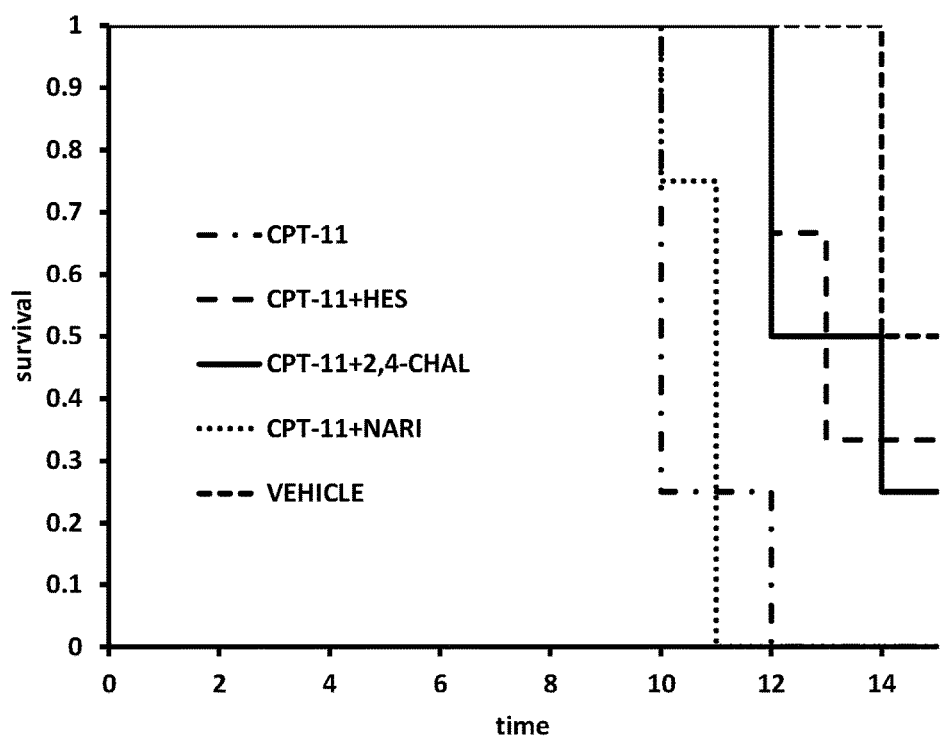
FIG. 1C is a plot of survival of tumor-bearing mice versus days after initiation of treatment with the indicated regimens. CPT-11=irinotecan, HES=hesperetin, 2,4-CHAL=2',4'-dihydroxychalcone, NARI=naringenin.

The CES2 inhibitor treatment groups were compared to the CPT-11 only group and to the vehicle control group. Four major parameters were examined to quantify the effect of CES2 inhibitors, namely, body weight change, presence of diarrhea, survival time, and average tumor size. The results are shown in FIGS. 1A, 1B, and 1C; and in Table 2 below.

TABLE 2

Percentage of mice having diarrhea

| Days after treatment | CPT-11 only | CPT-11 + HES | CPT-11 + 2,4-CHAL | CPT-11 + NARI | vehicle |
|---|---|---|---|---|---|
| 9  | 50 | 0  | 0  | 25 | 0 |
| 10 | 50 | 0  | 0  | 50 | 0 |
| 11 | 75 | 0  | 0  | 75 | 0 |
| 12 | 75 | 25 | 0  | 75 | 0 |
| 13 | 75 | 66 | 25 | 75 | 0 |
| 14 | 75 | 66 | 0  | 75 | 0 |

A significant delay of 3-4 days in the appearance of diarrhea was observed when administering hesperetin or 2',4' dihydroxychalcone in combination with CPT-11 to tumor bearing mice. More specifically, diarrhea occurred in the CPT-11 group on day 9 while the groups treated with CPT-11 plus hesperetin or 2',4' dihydroxychalcone did not develop diarrhea until day 12 and day 13, respectively. See Table 2.

The percentage of mice developing diarrhea was decreased in animals treated with CPT-11 and the CES2 inhibitor as compared to CPT-11 alone. Peak efficacy was apparent on day 12 when 75% of mice from the CPT-11 only group developed diarrhea staining while only 25% of mice in the hesperetin group and no mice in the 2',4' dihydroxychalcone group developed diarrhea. See Table 2.

No significant changes of anti-tumor efficacy, as evaluated by tumor growth, were found between the CPT-11 only group and the CPT-11+hesperetin, 2',4' dihydroxychalcone, and naringenin groups. See FIG. 1A.

Losses in body weight induced by CPT-11 treatment were reversed in groups treated with CPT-11 and hesperetin or with CPT-11 and 2',4' dihydroxychalcone. See FIG. 1B at 14-16 days of treatment.

Survival rates of treated animals were also improved by administering either hesperetin or 2',4' dihydroxychalcone together with CPT-11 as compared to CPT-11 alone. See FIG. 1C.

EXAMPLE 4

In Vivo Efficacy of CPT-11 Plus Hesperetin

Figure 2A:
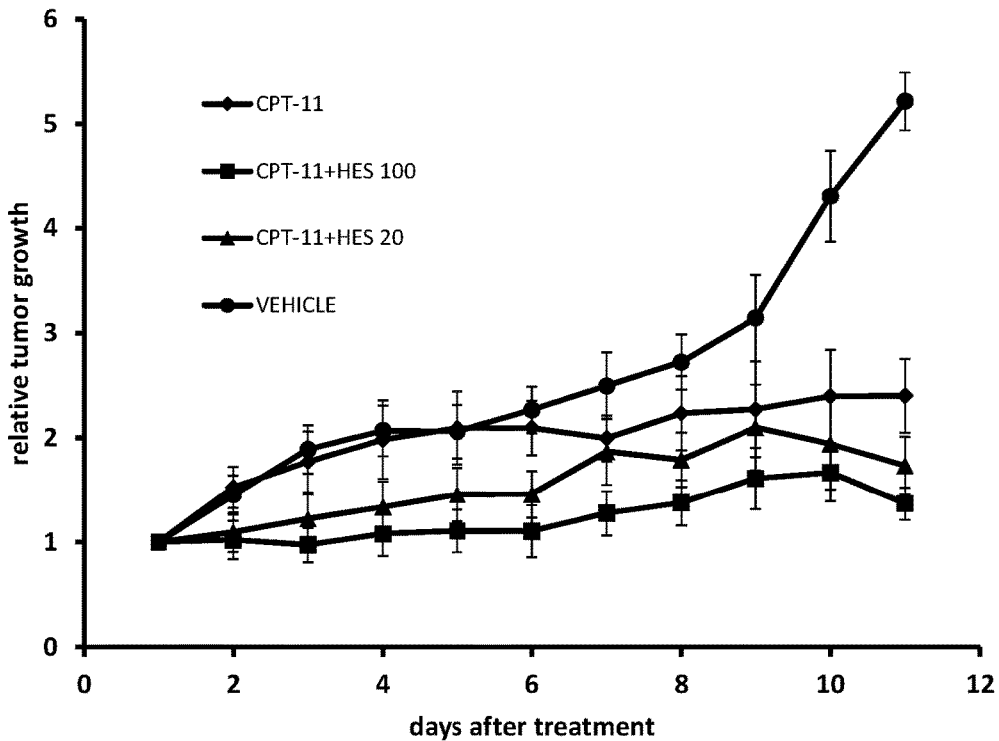
FIG. 2A is a plot of relative tumor growth in tumor-bearing mice versus day after initiation of treatment with the indicated regimens. Error bars represent SEM. CPT-11=irinotecan, HES 100=hesperetin at 100 mg/kg, HES 20=hesperetin at 20 mg/kg.
Figure 2B:
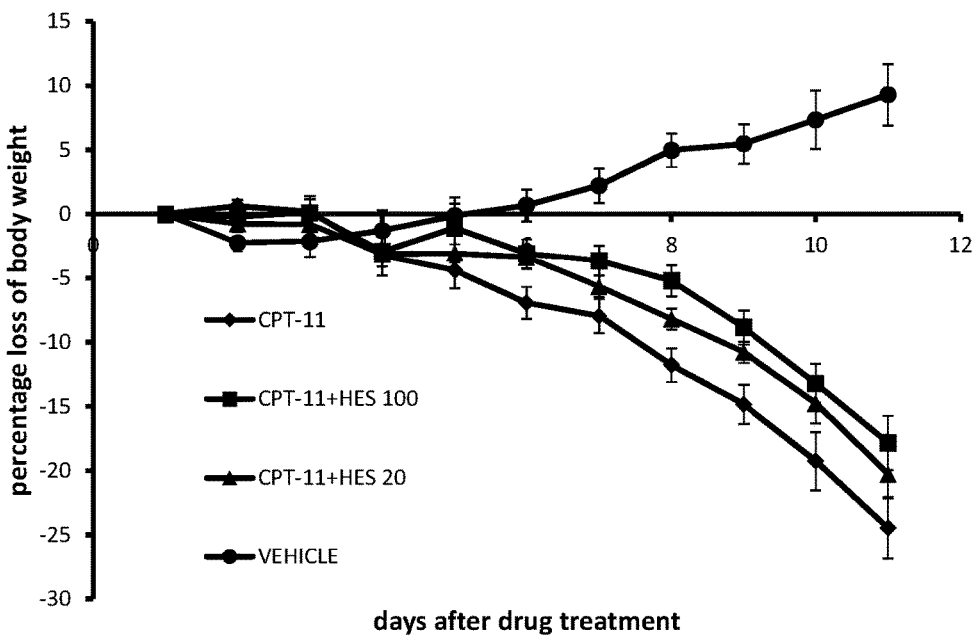
FIG. 2B is a plot of percentage change in body weight in the tumor-bearing mice versus day after initiation of treatment with the indicated regimens. Error bars represent SEM. CPT-11=irinotecan, HES 100=hesperetin at 100 mg/kg, HES 20=hesperetin at 20 mg/kg.
Figure 2C:
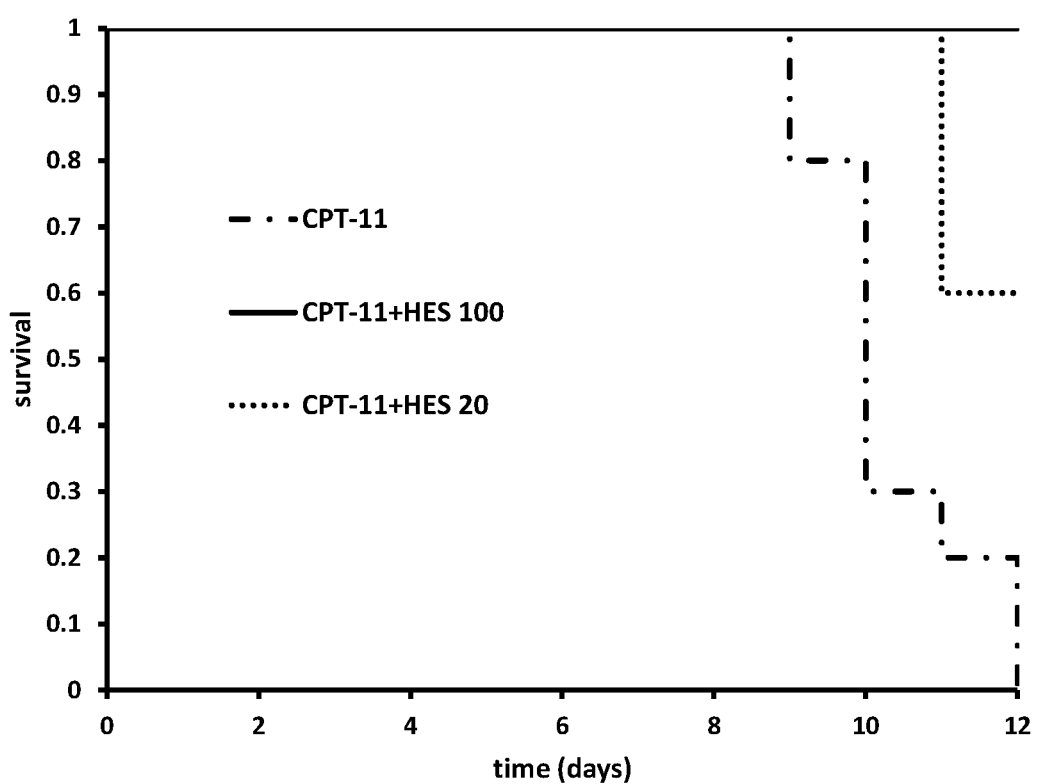
FIG. 2C is a plot of survival of tumor-bearing mice versus days after initiation of treatment with the indicated regimens. CPT-11=irinotecan, HES 100=hesperetin at 100 mg/kg, HES 20=hesperetin at 20 mg/kg.

The effect of different doses of hesperetin on development of CPT-11-induced diarrhea was tested using the same experimental protocol described in Example 3, supra. CPT-11 was administered together with hesperetin at either 20 mg/kg or 100 mg/kg. The results are shown in FIGS. 2A, 2B, and 2C; and in Table 3 below.

TABLE 3

Percentage of mice having diarrhea

| Days after treatment | CPT-11 | CPT-11 + Hes 100 mg/kg | Cpt-11 + Hes 20 mg/kg |
|---|---|---|---|
| 8  | 10 | 0 | 0  |
| 9  | 20 | 0 | 0  |
| 10 | 40 | 0 | 10 |
| 11 | 70 | 0 | 20 |
| 12 | 70 | 20 | 20 |

A hesperetin dose of 100 mg/kg delayed the onset of diarrhea to day 12 from day 10 as compared to a lower dose of 20 mg/kg. See Table 3. Importantly, both hesperetin doses significantly delayed the onset of diarrhea as well as reduced the number of animals exhibiting diarrhea as compared to CPT-11 alone. See Id.

The anti-tumor efficacy of CPT-11 was improved if co-administered together with either dose of hesperetin. See FIG. 1A.

Similarly, loss in body weight induced by CPT-11 administration was reduced by co-administration of hesperetin at both doses tested. See FIG. 2B.

Finally, survival of animals was improved by co-administering hesperetin and CPT-11 as compared to CPT-11 alone at both hesperetin doses. See FIG. 2C.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

The invention claimed is:

1. A method for treating diarrhea induced by a chemotherapy agent, the method comprising identifying a subject in need of treatment and administering to the subject a therapeutically effective amount of a first carboxylesterase 2 (CES2) inhibitor selected from the group consisting of hesperetin, naringenin, and 2',4'-dihydroxychalcone, wherein the chemotherapy agent is a camptothecin analogue.

2. The method of claim 1, wherein the camptothecin analogue is irinotecan, topotecan, 7-ethyl-10 hydroxycamptothecin (SN-38), liposomal encapsulated SN-38, polyethylene glycol-conjugated SN-38, PEG-polyglutamic acid micelle encapsulated SN-38, or PEG-cyclodextrin encapsulated SN-38.

3. The method of claim 2, further comprising administering an anti-emetic agent, an anti-motility agent, or a combination thereof.

4. The method of claim 1, wherein the first CES2 inhibitor is hesperetin.

5. The method of claim 4, wherein the camptothecin analogue is irinotecan, topotecan, SN-38, liposomal encapsulated SN-38, polyethylene glycol-conjugated SN-38, PEG-polyglutamic acid micelle encapsulated SN-38, or PEG-cyclodextrin encapsulated SN-38.

6. The method of claim 5, wherein the camptothecin analogue is irinotecan.

7. The method of claim 6, further comprising administering an anti-emetic agent, an anti-motility agent, or a combination thereof.

8. The method of claim 1, further comprising administering a second CES2 inhibitor different from the first CES2 inhibitor.

9. A method for treating cancer, the method comprising identifying a subject in need of treatment and administering to the subject a therapeutically effective amount of a chemotherapy agent and a carboxylesterase 2 (CES2) inhibitor selected from the group consisting of hesperetin, naringenin, and 2',4'-dihydroxychalcone, wherein the chemotherapy agent is a camptothecin analogue.

10. The method of claim 9, wherein the camptothecin analogue is irinotecan, topotecan, 7-ethyl-10 hydroxycamptothecin (SN-38), liposomal encapsulated SN-38, polyethylene glycol-conjugated SN-38, PEG-polyglutamic acid micelle encapsulated SN-38, or PEG-cyclodextrin encapsulated SN-38.

11. The method of claim 10, wherein the camptothecin analogue is administered by infusion and the CES2 inhibitor is administered orally.

12. The method of claim 11, further comprising administering a bacterial beta glucuronidase inhibitor.

13. The method of claim 9, wherein the CES2 inhibitor is hesperetin.

14. The method of claim 13, wherein the camptothecin analogue is irinotecan.

15. The method of claim 14, wherein the irinotecan is administered orally or by infusion and the hesperetin is administered orally.

16. The method of claim 15, further comprising administering a bacterial beta glucuronidase inhibitor.

17. The method of claim 11 wherein the CES2 inhibitor is 2',4'-dihydroxychalcone.

18. A composition for treating cancer, comprising a chemotherapy agent and a carboxylesterase 2 (CES2) inhibitor selected from the group consisting of hesperetin, naringenin, and 2',4'-dihydroxychalcone, wherein the chemotherapy agent is a camptothecin analogue.

19. The composition of claim 18, wherein the camptothecin analogue is irinotecan, topotecan, 7-ethyl-10 hydroxycamptothecin (SN-38), liposomal encapsulated SN-38, polyethylene glycol-conjugated SN-38, PEG-polyglutamic acid micelle encapsulated SN-38, or PEG-cyclodextrin encapsulated SN-38.

20. The composition of claim 19, wherein the CES2 inhibitor is hesperetin.

21. The composition of claim 18, wherein the CES2 inhibitor is hesperetin.

22. The composition of claim 18, wherein the CES2 inhibitor is naringenin.

23. The composition of claim 19, wherein the CES2 inhibitor is naringenin.

24. The composition of claim 18, wherein the CES2 inhibitor is 2',4'-dihydroxychalcone.

25. The composition of claim 19, wherein the CES2 inhibitor is 2',4'-dihydroxychalcone.

* * * * *